US00PP25769P2

(12) United States Plant Patent
Pounders et al.

(10) Patent No.: US PP25,769 P2
(45) Date of Patent: Aug. 4, 2015

(54) AZALEA PLANT NAMED 'AZ 47'

(50) Latin Name: *Rhododendron hybrida*
Varietal Denomination: AZ 47

(71) Applicants: The United States of America, as represented by the Secretary of Agriculture, Washington, DC (US); Capstone Plants Inc., Grand Saline, TX (US)

(72) Inventors: Cecil T Pounders, Poplarville, MS (US); James B Berry, Mineola, TX (US)

(73) Assignees: CAPSTONE PLANTS, INC., Grand Saline, TX (US), part interest; THE UNITED STATES OF AMERICA AS REPRESENTED BY THE SECRETARY OF AGRICULTURE, Washington, DC (US), part interest ( * ) Notice: Subject to any disclaimer, the term of this patent is extended or adjusted under 35 U.S.C. 154(b) by 176 days.

(21) Appl. No.: 13/987,581

(22) Filed: Aug. 9, 2013

(51) Int. Cl.
*A01H 5/00* (2006.01)

(52) U.S. Cl.
USPC ..... Plt./240

(58) Field of Classification Search
USPC ..... Plt./238, 240
See application file for complete search history.

*Primary Examiner* — Susan McCormick Ewoldt
(74) *Attorney, Agent, or Firm* — Penny J. Aguirre

(57) ABSTRACT

A new cultivar of Azalea named 'AZ 47', that is characterized by its repeat blooming habit, its floriferous blooming habit with fuchsia pink single flowers, its foliage that has been observed to be pest free, its high tolerance to heat and humidity when grown in Southern U.S.A., and its ability to be readily propagated by softwood stem cuttings with a high percentage of successful rooting.

2 Drawing Sheets

Botanical classification: *Rhododendron hybrida.*
Cultivar designation: 'AZ 47'.

BACKGROUND OF THE INVENTION

The present invention relates to a new and distinct cultivar of *Rhododendron* plant of hybrid origin, botanically known as *Rhododendron hybrida* 'AZ 47' and will be referred to hereafter by its cultivar name, 'AZ 47'. 'AZ 47' is a new cultivar of evergreen Azalea grown for use as a landscape plant.

The new cultivar was developed through an on-going breeding program conducted by the Inventors in Poplarville, Miss. The objectives of the breeding program are to develop new cultivars of Azalea that exhibit tolerance to environmental stresses and disease resistance combined with unique flower colors and extended bloom periods.

The new cultivar arose from a cross made in spring of 2005 between an unnamed plant received from a breeding program in Semmes, Ala., Ref. No. TD28, as the female parent, and 'Red Slippers' (not patented) as the male parent. The Inventors selected 'AZ 47' as a single unique plant amongst the seedlings that resulted from the above cross in 2007.

Asexual propagation of the new cultivar was first accomplished by softwood stem cuttings in Poplarville, Miss. in 2008 by one of the Inventors. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics 'AZ 47'. These attributes in combination distinguish 'AZ 47' as a new and distinct cultivar of Azalea.

1. 'AZ 47' is a repeat bloomer with a strong bloom period in late March to early April followed by a seconding bloom period in late July through October in Mississippi.
2. 'AZ 47' exhibits a floriferous blooming habit with fuchsia pink single flowers.
3. 'AZ 47' exhibits foliage that has been observed to be pest free.
4. 'AZ 47' exhibits a high tolerance to heat and humidity when grown in Southern U.S.A.
5. 'AZ 47' is readily propagated by softwood stem cuttings with a high percentage of successful rooting.

The female parent of 'AZ 47', Ref. No. TD28, differs from 'AZ 47' in having winter foliage that thins, in being less floriferous, and in having duller pink flowers. The male parent, 'Red Slippers', differs from 'AZ 47' in having less cold hardiness, in blooming earlier resulting in susceptibility to frost damage to its flowers, and in having a weaker root system. 'AZ 47' can also be most closely compared to the cultivars 'Southern Summer Sun' (not patented), 'AZ 32' (U.S. patent application Ser. No. 13/987,578) and 'RLH1-1P2' (U.S. Plant Pat. No. 21,562). All are similar to 'AZ 47' in having repeat blooming habits. 'RLH1-1P2' differs from 'AZ 47' in having less tolerance to heat and full sun and in having poor tolerance to rain and humidity during spring flowering. 'AZ 32' differs from 'AZ 47' in having flowers that are brighter red-purple in color with petals that have more wavy margins. 'Southern Summer Sun' differs from 'AZ 47' in being more difficult to propagate, in having less cold hardiness, and in having a more open growth habit.

BRIEF DESCRIPTION OF THE DRAWINGS

The accompanying colored photograph were taken of 18 month-old plants of the new cultivar as grown outdoors in three-gallon containers in a greenhouse in Grand Saline, Tex.

The photograph in FIG. 1 provides a view of 'AZ 47' in bloom.

Figure 1:
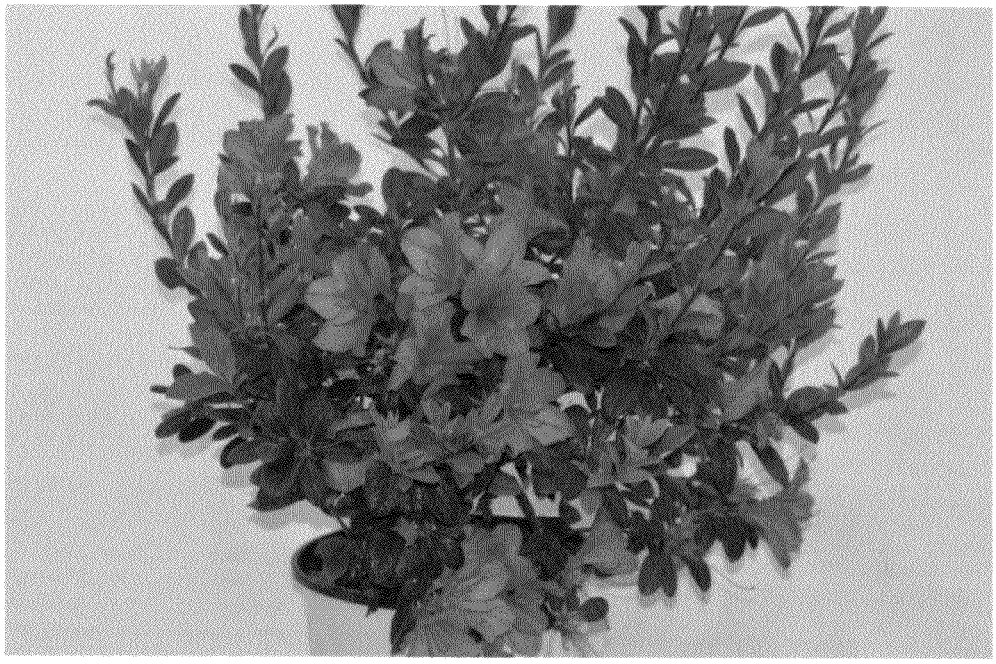
Figure 2:
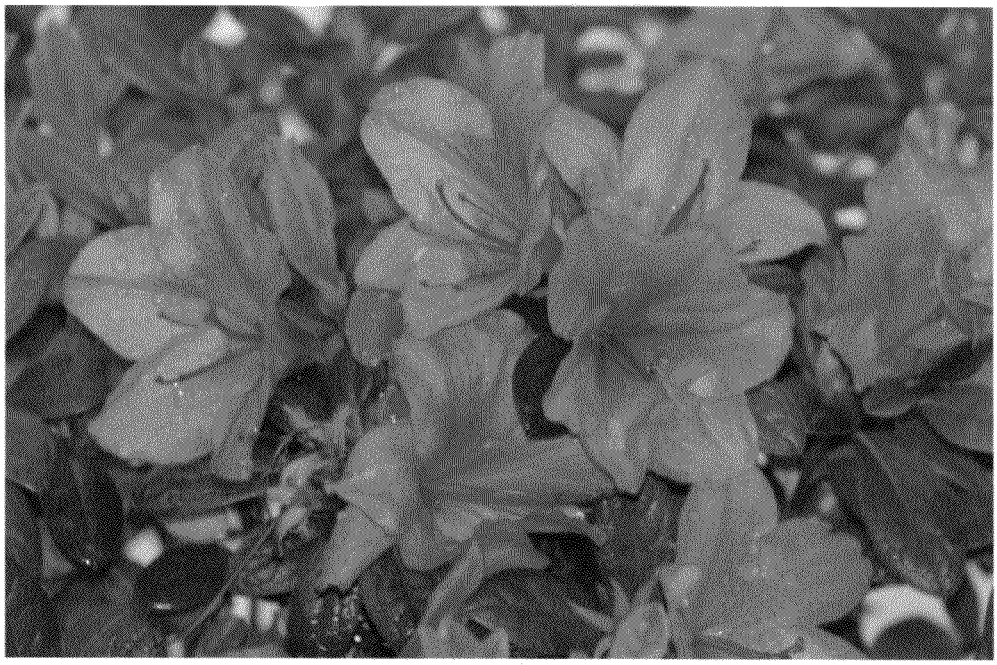

The photograph in FIG. 2 provides a close-up view of the inflorescences of 'AZ 47'.

The colors in the photographs are as close as possible with the digital photography and printing techniques utilized and the color codes in the detailed botanical description accurately describe the new Azalea.

DETAILED BOTANICAL DESCRIPTION OF THE PLANT

The following is a detailed description of 18 month-old plants of the new cultivar as grown outdoors in three-gallon containers in a greenhouse in Grand Saline, Tex. The phenotype of the new cultivar may vary with variations in environmental, climatic, and cultural conditions, as it has not been tested under all possible environmental conditions. The color determination is in accordance with The 2007 RHS Colour Chart of The Royal Horticultural Society, London, England, except where general color terms of ordinary dictionary significance are used.

General characteristics:

*Blooming period*.—Late March/early April and late August to September in Southern Mississippi, USA.

*Plant type*.—Evergreen shrub.

*Plant habit*.—Upright and dense.

*Height and spread*.—Reaches 56 cm in height and 45 cm in spread.

*Cold hardiness*.—At least in U.S.D.A. Zones 7, stems and flower buds that are resistant to cold damage when exposed to temperatures down to 14° F.

*Diseases*.—Resistance to common azalea pests is equivalent or better than commonly planted azalea clones.

*Pests*.—Foliage has been observed to be pest free under the conditions grown.

*Environmental conditions*.—Has been observed to be highly tolerant to high heat and humidity in southern U.S.A.

*Root description*.—Abundant, fibrous, white, well branched, moderately dense.

*Propagation*.—Softwood stem terminal cuttings, readily propagated readily propagated with a high percentage of successful rooting.

*Growth rate*.—Vigorous.

Stem description:

*Shape*.—Round.

*Stem color*.—New growth; 53A, mature wood; 165A.

*Stem size*.—Main stems; an average of 19 cm in length and 1 cm in width, lateral stems; an average of 40 cm in length and 3 mm in diameter.

*Stem surface*.—New growth; very pubescent, 1 mm in length matching stem color, mature wood; exfoliating.

*Stem aspect*.—Held at an average angle of 5 to 10° (0°=vertical).

*Stem strength*.—Strong.

*Branching*.—Self-branching, an average of 5 main stems and up to 9 lateral branches per main stem in a one-container.

*Internode*.—Average of 2 cm.

Foliage description:

*Leaf shape*.—Oblanceolate.

*Leaf division*.—Simple.

*Leaf base*.—Cuneate.

*Leaf apex*.—Obtuse.

*Leaf venation*.—Pinnate, upper and lower surface N144A with an overlay of N34 in color, both surfaces moderately covered with stiff pubescence, upper surface pubescence N170A, lower surface pubescence 170A in color.

*Leaf margins*.—Entire.

*Leaf attachment*.—Petiolate.

*Leaf arrangement*.—Alternate.

*Leaf orientation*.—Held horizontal to upright.

*Leaf aspect*.—Cupped downward.

*Leaf surface*.—Upper and lower surface coriaceous, cartilaginous, and shiny.

*Leaf color*.—Young leaves upper and lower surface; 144B, mature leaves upper surface; 137A, mature leaves lower surface; 146B.

*Leaf size*.—Average of 3.5 cm in length, and 1.7 cm in width.

*Leaf quantity*.—Up to 32 leaves per lateral branch 30 cm in length.

*Petioles*.—Average of 1 cm in length and 2 mm in diameter, 11A with a thin middle overlay of 42B in color, covered with moderate pubescence; 1 mm in length and 42B in color.

Flower description:

Inflorescence type.—Flowers are solitary.

*Lastingness of flowers*.—About 10 days, self-cleaning.

*Flower size*.—An average of 2 cm in depth and 5 cm in diameter.

*Flower fragrance*.—None.

*Flower shape*.—Rotate.

*Flower number*.—2 to 3 per lateral stem.

*Flower aspect*.—Upright or outward.

*Flower bud*.—Ovate in shape, an average of 2 cm in depth and 1.2 cm in diameter, apex; acute, color; 58B with sepal portion 145B.

*Flower attachment*.—Peduncle.

*Petal number*.—5.

*Petal shape*.—Elliptic to slightly ovate.

*Petal color*.—58B with freckles on lower 2/3 58A in color on upper surface and 58B on lower surface.

*Petal surface*.—Both surfaces smooth.

*Petal margins*.—Slightly wavy and very slightly crenate.

*Petal apex*.—Obtuse.

*Petal base*.—Fused.

*Petal size*.—Average of 2.5 cm in length and 2 cm in width.

*Sepal number*.—5.

*Sepal shape*.—Lanceolate.

*Sepal margin*.—Entire.

*Sepal size*.—Average of 5 mm in length and 3 mm in width.

*Sepal aspect*.—Upright, lower 50% fused.

*Sepal surface*.—Pubescent on upper and lower surface.

*Sepal apex*.—Acute-slightly acuminate.

*Sepal base*.—Fused.

*Sepal color*.—145B on upper and lower surface.

*Calyx*.—Campanulate in shape, average of 5 mm in length and 1.5 cm in diameter.

*Peduncles*.—An average of 1 cm in length and 2 mm in diameter, 53A in color, flexible strength, slightly pubescent surface, held upright.

Reproductive organs:

*Gynoecium*.—Pistils, up to 4 cm in length, stigmas; club-shaped, an average of 5, and N79B in color, style; 4.5 cm in length and 58A in color, ovary; 7 mm in length and 6 mm in width, 150C in color and is completely covered by the base of the pistil style.

*Androecium*.—Stamens; average of 5, 3 cm in length, filament 59C in color, anthers; 59A in color, pollen is moderate in quantity, of unknown fertility, and 11C in color.

*Fruit/seeds*.—Seed pod an average of 12 mm in length and 5 mm in width, a blend of 133A to 199C in color.

It is claimed:

1. A new and distinct cultivar of Azalea plant named 'AZ 47' as herein illustrated and described.

* * * * *